US010406382B2

United States Patent
Humber et al.

(10) Patent No.: US 10,406,382 B2
(45) Date of Patent: Sep. 10, 2019

(54) DUAL-AXIS RING GANTRY RADIOTHERAPY SYSTEMS

(71) Applicant: Varian Medical Systems, Inc., Palo Alto, CA (US)

(72) Inventors: David Humber, Los Gatos, CA (US); Josh Star-Lack, Palo Alto, CA (US); Stanley Mansfield, Sunnyvale, CA (US); Ross Hannibal, Saratoga, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 216 days.

(21) Appl. No.: 15/494,046

(22) Filed: Apr. 21, 2017

(65) Prior Publication Data

US 2018/0304098 A1    Oct. 25, 2018

(51) Int. Cl.
*A61N 5/10* (2006.01)
*A61B 6/03* (2006.01)
*A61B 6/00* (2006.01)

(52) U.S. Cl.
CPC ............ *A61N 5/1037* (2013.01); *A61B 6/035* (2013.01); *A61B 6/4085* (2013.01); *A61B 6/4441* (2013.01); *A61B 6/4447* (2013.01); *A61N 5/1082* (2013.01); *A61B 6/547* (2013.01); *A61N 5/1049* (2013.01); *A61N 2005/1059* (2013.01); *A61N 2005/1061* (2013.01); *A61N 2005/1089* (2013.01)

(58) Field of Classification Search
CPC ................ A61N 5/1037; A61N 5/1082; A61N 2005/1059; A61N 2005/1061; A61N 2005/1089; A61N 5/1049; A61B 6/035; A61B 6/4441; A61B 6/4447; A61B 6/4085; A61B 6/547
See application file for complete search history.

(56) References Cited

U.S. PATENT DOCUMENTS

| | | | |
|---|---|---|---|
| 2,167,116 | A | 7/1939 | Kieffer |
| 2,640,159 | A | 5/1953 | Gerneth |
| 2,781,454 | A | 2/1957 | Green et al. |
| 2,793,296 | A | 5/1957 | Peterson |
| 2,890,349 | A | 6/1959 | Huszar |

(Continued)

OTHER PUBLICATIONS

PCT, International Search Report and Written Opinion of International Searching Authority in PCT/US2018/024342, dated Aug. 6, 2018, 10 pages.

*Primary Examiner* — Christine H Matthews
*Assistant Examiner* — Joshua Daryl D Lannu
(74) *Attorney, Agent, or Firm* — IP Legal, Varian Medical Systems, Inc.

(57) ABSTRACT

A radiation system includes a radiation source providing therapeutic radiation, a first gantry supporting a second gantry carrying the radiation source. The first gantry is rotatable about a first axis passing through an isocenter, thereby allowing the radiation source to aim therapeutic radiation at a target volume from a plurality of locations in a first plane. The second gantry carrying the radiation source is rotatable about a second axis passing through the isocenter non-parallel with the first axis, thereby allowing the radiation source to aim therapeutic radiation at the target volume from a plurality of locations in a second plane non-coplanar with the first plane.

33 Claims, 5 Drawing Sheets

(56) References Cited

U.S. PATENT DOCUMENTS

| | | |
|---|---|---|
| 3,349,242 A | 10/1967 | Braestrup |
| 3,892,967 A | 7/1975 | Howarth |
| 4,653,083 A | 3/1987 | Rossi |
| 5,427,097 A | 6/1995 | Depp |
| 5,894,503 A | 4/1999 | Shepherd |
| 6,461,039 B1 | 10/2002 | Klotz |
| 6,789,941 B1 | 9/2004 | Grady |
| 6,865,254 B2 | 3/2005 | Nafstadius |
| 6,969,194 B1 | 11/2005 | Nafstadius |
| 7,085,347 B2 | 8/2006 | Mihara |
| 7,188,999 B2 | 3/2007 | Mihara |
| 7,295,648 B2 | 11/2007 | Brown |
| 8,536,547 B2 | 9/2013 | Maurer, Jr. |
| 8,546,773 B2 | 10/2013 | Stokes |
| 8,664,618 B2 | 3/2014 | Yao |
| 8,750,453 B2 | 6/2014 | Cheng |
| 8,917,813 B2 | 12/2014 | Maurer, Jr. |
| 8,934,605 B2 | 1/2015 | Maurer, Jr. |
| 9,155,912 B2 | 10/2015 | Yu |
| 9,687,200 B2 | 6/2017 | Maurer, Jr. |
| 2004/0005027 A1* | 1/2004 | Nafstadius ........... A61N 5/1049 378/65 |
| 2011/0085640 A1 | 4/2011 | Fadler |
| 2012/0189102 A1 | 7/2012 | Maurer, Jr. et al. |
| 2013/0144104 A1 | 6/2013 | Adler et al. |
| 2013/0256551 A1 | 10/2013 | Yao |
| 2014/0171725 A1 | 6/2014 | Adler et al. |
| 2016/0303400 A1 | 10/2016 | Mauer |
| 2016/0325119 A1 | 11/2016 | Yu |

\* cited by examiner

DUAL-AXIS RING GANTRY RADIOTHERAPY SYSTEMS

TECHNICAL FIELD

Embodiments of this disclosure relate generally to radiation systems and methods. In particular, various embodiments of a radiation system which allows a radiation source to rotate about at least two axes of rotation to provide a wide range of coplanar and non-coplanar beam angles are described.

BACKGROUND

Radiation systems are used in a variety of applications including treatment of patients. In operation, a radiation source may be moved using a rotating gantry to aim radiation beams at a tumor site from multiple angles. One type of gantry is in the shape of a C-arm, on which the radiation source is mounted in a cantilevered manner and rotated about an axis passing through the tumor site. Another type of gantry is in the shape of a toroid or ring, which has a central opening or bore to allow the patient's body to extend through. The radiation source is mounted on the perimeter of the ring and rotated about an axis passing through the tumor site.

Radiation systems using a C-arm or ring gantry have complementary strengths and weaknesses. A major advantage of C-arm systems is that they allow for implementation of non-coplanar treatments through the use of a combination of different gantry rotation angles, multi-leaf collimator (MLC) adjustments, and patient table maneuvers. These treatments can be either fixed-field or arc-based, conformal or modulated. Disadvantages of C-arm systems are that, due to their open geometry, collision avoidance can be very complicated, cone beam computed tomography (CBCT) scan times are long (on the order of 30 seconds to 1 minute) in part due to regulatory requirements, whole-body treatments are not enabled, and more elaborate room shielding may be required to block radiation not intercepted by the C-arm apparatus itself. Conversely, ring gantry systems support rapid CBCT acquisitions, do not require complicated collision avoidance systems, enable whole body treatments, and are more conducive to self-shielding. However, a major limitation of ring gantry systems is that they do not readily allow for non-coplanar treatments.

SUMMARY

Provided by this disclosure is a radiation system that uniquely combines the complementary strengths of C-arm and ring gantry radiation systems. The disclosed radiation system can provide non-coplanar treatment capabilities, rapid cone beam computed tomography (CBCT), simplified collision avoidance, whole-body treatments, and more opportunities for self shielding, etc. The disclosed radiation system can provide for a wide range of coplanar and non-coplanar source angles by employing two axes of rotation.

In an exemplary embodiment, the first axis of rotation may be fixed e.g. along the superior-inferior (SI) direction of the patient, who may be positioned prone or supine on a patient table, either head-first or feet-first.

Rotation of the radiation source about the first axis can be provided by a first gantry, which may be supported by a front gantry bearing and a rear gantry bearing, or alternatively, by a single gantry bearing located either in the front or rear end.

In an exemplary embodiment, the first gantry may comprise two sections of parallel "truck-rings" each mounting curved rail bearings. Rotation of the radiation source about the second axis may be provided by a second gantry or truck riding on the curved rail bearings of the first gantry in a circular orbit. Together, the first and second gantries can be used to aim treatment beams at the patient lying on the patient support. The second gantry may carry major components of the treatment head, including e.g. a linear accelerator (LINAC), a magnetron, and an ion chamber/multi-leaf collimator/target assembly, and a modulator. In alternative embodiments, the modulator may be mounted to the first gantry and rotates around the first axis of rotation. As such, cabling between the modulator and LINAC may be arranged to accommodate the complete range of motion around the second axis of rotation.

The absolute direction of the second axis of rotation may depend on the first gantry rotation angle. By way of example, when the first gantry angle is 0 or 180 degrees (12 or 6 o'clock position), the second axis of rotation is directed along the left-right (LR) axis of the patient. When the first gantry angle is 90 or 270 degrees (3 or 9 o'clock position), the second axis of rotation is directed along the anterior-posterior (AP) axis of the patient.

The radiation system may include paired stereo kV sources and imagers that can be coupled to the sides of the truck-rings of the first gantry. The rotation of the paired kV sources and imagers about the first axis via the first gantry allows for acquisition of CBCT data for patient set-up and/or adaptive treatment planning. The kV imagers can be shifted laterally to enable acquisition of data in "half-fan mode" to enlarge the field-of-view (FOV). By operating the kV source-imager pairs simultaneously, it is possible to reduce the rotation angle needed for acquiring an adequate set of CBCT data. The kV source-imager pairs can also be used to acquire projection radiographs or digital tomosynthesis data before treatment for patient set-up or adaptive planning. Imaging data can also be acquired during treatment for intrafraction motion management.

The radiation system may further include a mega-voltage (MV) electronic portal imaging device (EPID) and a beamstop, which may be mounted to the second gantry in a location opposite to the treatment head. Alternatively, the EPID and beamstop may be carried by a separate truck which is supported by the first gantry. The EPID/beamstop assembly can be shifted laterally in a manner similar to the kV imagers for half-fan CBCT acquisitions to enlarge the FOV. In embodiments where e.g. a full range of motions of the treatment source are exploited to achieve large caudal and/or cranial angles, it may be advantageous that the separate truck carrying the EPID/beamstop assembly is not positioned opposite to the treatment source at all times. Hence, in some embodiments, the truck for the EPID/beamstop assembly may be powered by a separate drive, thereby giving the system maximum flexibility of motion by allowing the EPID/beamstop assembly to independently avoid interference with obstacles e.g. the inner bore or the first and/or second gantries. In embodiments where the treatment source and EPID support structures are decoupled, extra interlocks and position sensing devices, e.g. shaft encoders, potentiometers or the like, may be incorporated into the radiation system to ensure that the EPID and treatment source support structures are where they should be.

The radiation system may be provided with a scheme of covering to protect the patient from its inner workings and present a cosmetically pleasing enclosure. An inner tube covering the bore of the radiation system may have multiple sections such as two, three, or more sections. By way of example, the front and rear sections of the tube may be in the form of cylinders which may have same or different radii. The middle section may bulge out at the isocenter plane to permit for a more open feel. To increase the cranial non-coplanar angle, the rear section may be designed so that it can be moved out of the way to allow the second gantry carrying the treatment source to move into the area where the bore cover was. One means for achieving this is for the rear section to be slid in or out of the way along the superior direction (when the patient is laying head first). Alternatively, the rear section may include two hemi-cylinders that can rotate against each other along the superior-inferior axis of the patient. The hem i-cylinders can be coupled to the support bearing of the system so that they also rotate in tandem with the truck-rings of the first gantry to allow for a multiplicity of non-coplanar rotation angles along the first axis to be obtained.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of a radiation system are described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" etc. may be used to distinguish one element from another. The use of the term "first" or "second" should not be construed as in any particular order unless the context clearly dictates otherwise. Further, the singular form of "first" and "second" include plural references unless the context clearly dictates otherwise.

As used herein, the term "gantry" refers to a structure configured to carry or support a radiation source and rotatable about an axis passing through the isocenter of a radiation system.

As used herein, the term "radiation source," which may be used interchangeably with the term "treatment source" or "treatment head," refers to a source that generates therapeutic radiation including but not limited to x-rays, gamma-rays, protons, heavy ions, and electrons, etc. By way of example, a radiation source may include a target or metallic component which produces radiation of x-rays upon impingement of electrons from an electron accelerator. Therapeutic radiation generally has an energy level ranging from 0.2 to 20 megavoltage (MV).

As used herein, the term "imaging radiation source" or "imaging source" refers to a source operable to produce radiation that is suitable for imaging. Radiation from an imaging source generally has an energy level in the order of kilovoltage (KV), which is suitable for a receptor or imager to produce images with a good contrast and resolution for diagnostic purposes. It should be noted that therapeutic radiation from a radiation source may also be used with a suitable imaging device to produce images for patient set up, treatment monitoring, and in-treatment planning etc.

Disclosed herein is a novel radiation system that can provide a wide range of coplanar and non-coplanar moving trajectories for a radiation source in delivering therapeutic radiation to a target volume from a variety of angles. One or more imaging systems may be included in the radiation system to allow for real time stereoscopic imaging.

In an exemplary embodiment, a radiation system of the disclosure comprises a radiation source providing therapeutic radiation and a first gantry supporting a second gantry carrying the radiation source. The first gantry is rotatable about a first axis passing through the isocenter of the radiation system, thereby allowing the radiation source carried by the second gantry to aim therapeutic radiation at a target volume from a plurality of locations in a first plane. The second gantry carrying the radiation source is rotatable about a second axis passing through the isocenter non-parallel with the first axis, thereby allowing the radiation source to aim therapeutic radiation to the target volume from a plurality of locations in a second plane non-coplanar with the first plane.

In some embodiments, the first gantry may comprise a ring structure. The ring structure may be either a closed or complete ring structure, or an open or partial ring structure, providing a circular or arc orbit. The first gantry may comprise a single ring structure which may be either closed or open. The first gantry may also comprise a pair of parallel rings each of which may be either closed or open. The second gantry carrying the radiation source may ride on the ring structure of the first gantry, or move along the circular or arc orbit of the ring structure of the first gantry.

In some embodiments, the first gantry may comprise one or more beam members which may be rotated about the first axis. The one or more beam members may be either linear or arcuate. The radiation source may be supported by one or more of the beam members. The radiation source may be further linearly translated on the beam member(s) or rotated about a second axis, depending on the shape or configuration of the beam member(s). The linear movement of the radiation source on the beam member(s) allows the radiation source to be positioned closer to the patient, providing for higher dose rate. This would also allow for more space above the treatment head below the cover of the radiation system so that a larger or more powerful radiation source may be used. In some embodiments, a tilting mechanism may be used to allow the treatment head to tilt, allowing therapeutic radiation to aim at the target volume from the various locations.

In an exemplary embodiment, the first gantry may comprise a ring structure arranged substantially in parallel with the first axis. The second gantry may be moveable on the ring structure to rotate about the second axis substantially perpendicular to the ring structure.

The ring structure of the first gantry may be rotatably supported by a first support at a first end and a second support at a second end. Each of the first and second supports may comprise an annular ring structure arranged substantially perpendicular to the ring structure of the first gantry. Alternatively, the ring structure of the first gantry may be supported by a single support having an annular ring structure arranged substantially perpendicular to the ring structure of the first gantry.

The ring structure of the first gantry may comprise a first ring and a second ring spaced apart from each other and substantially in parallel with the first axis. Guides such as curved rail bearings may be mounted on the first and second rings to allow the second gantry to ride on to rotate about the second axis.

In some embodiments, the radiation system may include a first imaging system coupled to and moved with the first gantry. The first imaging system may include an imaging source and an imager. The imager of the first imaging system may be laterally movable relative to the imaging source of the first imaging system. Alternatively, the imager may be rigidly coupled to the first gantry.

In some embodiments, the radiation system may further include a second imaging system coupled to and moved with the first gantry. The second imaging system may include an imaging source and an imager. The imager of the second imaging system may also be laterally movable relative to the imaging source of the second imaging system. In an exemplary embodiment, the locations of the imaging sources of the first and second imaging systems may be arranged such that radiation beams from the imaging sources of the first and second imaging systems form a non-zero angle subtended from the isocenter as viewed from an end along the first axis. The non-zero angle may be fixed. In some embodiments, the non-zero angle can be adjusted by adjusting the locations of the imaging sources of the first and/or second imaging systems.

In some embodiments, the radiation system may further comprise an electronic portal imaging device (EPID) configured to acquire images with the radiation source. The EPID may be separately movable independent of the second gantry carrying the radiation source. Alternatively, the EPID may be rigidly coupled to the second gantry and rotated with the radiation source in synchrony.

In some embodiments, the radiation system may include an enclosure covering the first gantry, the second gantry, and the radiation source. A portion of the enclosure may define an inner bore along the first axis to allow at least a portion of a subject containing the target volume to extend through. The portion of the enclosure defining the inner bore may include a generally tubular structure. In some embodiments, at least a portion of the generally tubular structure is removable to allow the second gantry carrying the radiation source to move into the space occupied or enclosed by the portion of the tubular structure. In some embodiments, the generally tubular structure may include a first end section, a second end section, and a middle section between the first and second sections. The first and second end sections may be generally cylindrical. The third section may bulge out in a plane passing through the isocenter. In some embodiments, at least one of the first and second end sections includes a first hemi-cylindrical component and a second hemi-cylindrical component. The first and second hemi-cylindrical components may be rotatable against each other to open the generally tubular structure, thereby allowing the second gantry carrying the radiation source to move into the space occupied or enclosed by the first or second hemi-cylindrical component.

Figure 1A:
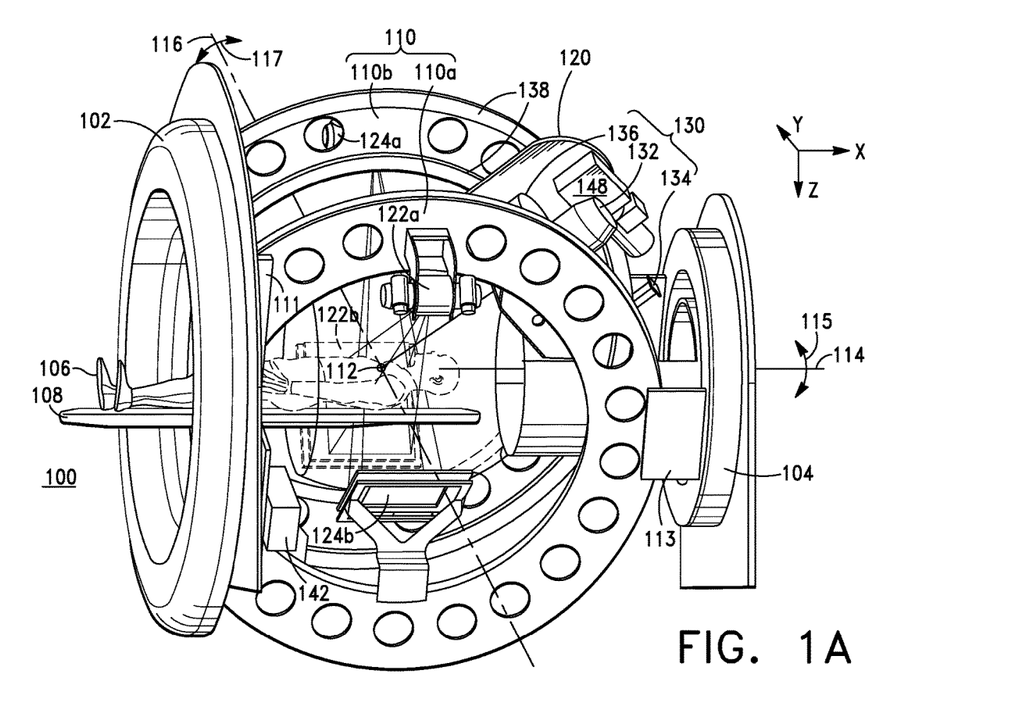
FIG. 1A illustrates a side view of an exemplary radiation system according to embodiments of the disclosure.
Figure 1B:
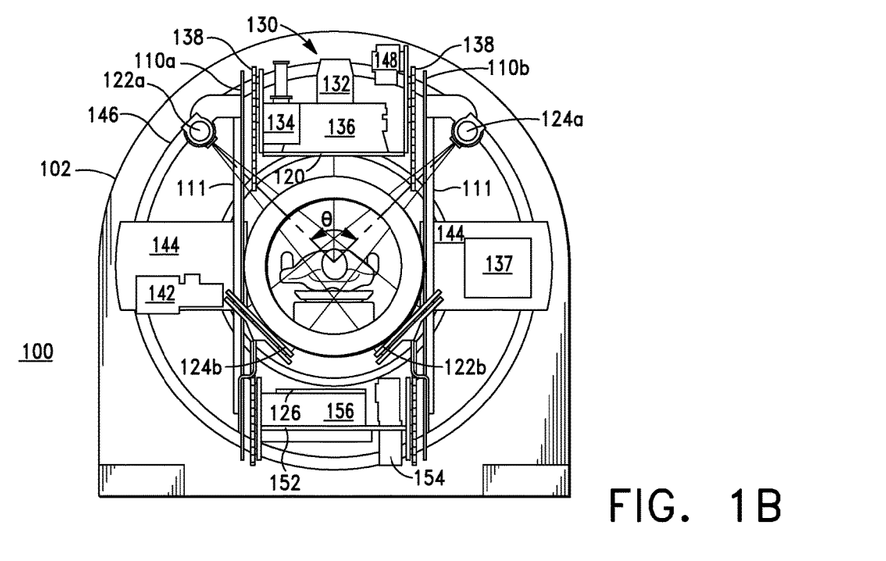
FIG. 1B illustrates an end view of the radiation system illustrated in FIG. 1A.

Referring to FIGS. 1A-1B, an exemplary radiation system 100 will be now described. As shown, the exemplary radiation system 100 may include a first gantry 110 rotatably supported by a first support 102 and a second support 104, a second gantry 120 riding on the first gantry 110, and a treatment head 130 carried or supported by the second gantry 120. A subject, e.g. a patient 106, is supported on a table 108 and positioned such that a target volume to be irradiated is located at the isocenter 112 of the radiation system 100. The first gantry 110 is rotatable about a first axis 114 passing through the isocenter 112, as indicated by arrow 115. The second gantry 120 carrying the treatment head 130 is rotatable about a second axis 116 passing through the isocenter 112, as indicated by arrow 117. The radiation system 100 may also include a first imaging system 122 comprising an imaging source 122a and an imager 122b, and optionally a second imaging system 124 comprising an imaging source 124a and an imager 124b. An electronic portal imaging device (EPID) 126 may also be included in the radiation system 100. The radiation system 100 may be controlled by a control (not shown), which may be programmed or configured to provide control signals for operation of the first and second gantries 110, 120, treatment head 130, imaging systems 122, 124, and the EPID 126, etc.

The treatment head 130 operates to generate therapeutic radiation. An exemplary treatment head 130 as shown may include a linear accelerator (LINAC) 132, a magnetron 134, and a target, multi-leaf collimator (MLC) and an ion chamber assembly 136. The function and construction of a linear accelerator (LINAC), magnetron, target, MLC, and ion chamber are known and therefore their detailed description and illustration are omitted herein for clarity of description of embodiments of the disclosure. Briefly and generally, a LINAC accelerates electrons emitted from an electron source. A magnetron provides microwave energies for the LINAC to accelerate electrons. A target produces radiation of x-rays upon impingement of accelerated electrons. An MLC includes a plurality of beam blocking or shaping leaves each of which can be independently moved in and out of a radiation beam to modify the beam shape, size, or intensity etc. An ion chamber monitors the parameters of a radiation beam. In various embodiments, the treatment head 130 may be designed to provide therapeutic radiation e.g. x-rays having an energy level in the order of megavoltage (MV), ranging e.g. from 0.2 to 20 MV. In various embodiments, the treatment head 130 may operate in either a photon mode or an electron mode. In a photon mode operation, the target may be placed in the beam path to produce x-rays, which may be then collimated and/or modulated to provide a desired beam profile for treatment. In an electron mode operation, the target may be moved out of the beam path to allow an electron beam to pass unimpeded, which may be then scattered and/or collimated to provide a desired beam profile for treatment. Therefore, in various embodiments, the treatment head 130 may include a positioning device for moving the target into and out of the beam path for photon and electron mode operations. It should be noted that the treatment head 130 may also be designed to provide other types of radiation such as protons. In some embodiments, the treatment head may include radioactive isotopes such as cobalt-60 as a therapeutic radiation source.

The first gantry 110 operates to rotate the second gantry 120 carrying the treatment head 130 about the first axis 114, as indicated by arrow 115. The rotation of the first gantry 110 about the first axis 114 allows the treatment head 130 to be positioned at a plurality of locations in a first plane, thereby allowing therapeutic radiation to aim at the target volume from a plurality of directions or angles. As shown, the first gantry 110 may rotate about the superior-inferior (SI) axis of the patient 106, when the patient 106 is positioned prone or supine on the patient table 108 either head-first or feet-first, allowing the treatment head 130 to deliver therapeutic radiation to the target volume from a plurality of locations in a plane coplanar with a transverse plane of the patient 106. For ease of description, the plurality of locations of the treatment head 130 in a plane coplanar with a transverse or axial plane of the patient 106 may be collectively referred to as coplanar locations. The first gantry 110 may rotate about the first axis 114 either clockwise and/or counterclockwise, allowing the treatment head 130 to be positioned at any angle between zero and 360 degrees with respect to a vertical axis passing through the isocenter 112, as viewed along the first axis 114, thereby allowing therapeutic radiation to aim at the target volume from any angle between zero and 360 degrees. In some embodiments, the first axis of rotation 114 of the first gantry 110 may be fixed.

The exemplary first gantry 110 shown in FIGS. 1A-1B comprises a ring structure including e.g. a first ring structure 110a and a second ring structure 110b arranged side by side or substantially in parallel. The first and second ring structure 110a, 110b may have a similar structure or configuration. The first and second ring structures 110a, 110b may be orientated in a direction substantially in parallel with the first axis 114 about which the first gantry 110 rotates. The first and second ring structures 110a, 110b may be spaced apart such that the patient 106 can be positioned in the space between the first and second ring structures 110a, 110b. The first and second ring structures 110a, 110b may be secured or rotated as a unit.

Still referring to FIGS. 1A-1B, each of the first and second ring structures 110a, 110b may include a side surface on which various devices or components such as imaging sources 112a, 124a, imagers 122b, 124b, etc. may be mounted, as will be described in greater detail below. Each of the first and second ring structures 110a, 110b may include a relatively large central opening to allow radiation beams from the imaging sources 122a, 124a to arrive at the patient 106, and allow radiation that penetrates through the patient 106 to deposit on the imagers 122b, 124b, without obstruction. The first and second ring structures 110a, 110b may be arranged such that their side surfaces are substantially in parallel with the first axis 114, e.g. the patient's superior-inferior direction. On each of the first and second ring structures 110a, 110b may be mounted guides such as curved rail bearings 138, which allow the second gantry 120 carrying the treatment head 130 to ride on and rotate about the second axis 116, as will be described in greater detail below.

The rotation of the first gantry 110 may be actuated by a drive system 142. As shown, the drive system 142 may move stages 144 along circular rail bearings 146 mounted on the first support 102, causing the first and second ring structures 110a, 110b of the first gantry 110 coupled to the stages 144 to rotate about the first axis 114. As shown, the first and second ring structures 110a, 110b may be coupled to the stages 144 via members 111. Alternatively, a drive system may move stages along circular rail bearings on the second support 104, causing the first and second ring structures 110a, 110b to rotate about the first axis 114. As shown in FIG. 1A, the first and second ring structures 110a, 110b may be coupled to the second support 104 via plate members 113. Any other suitable mechanisms may be used to actuate rotation of the first and second ring structures 110a, 110b of the first gantry 110.

The first and second ring structures 110a, 110b may be either a closed or an open ring structure providing a circular or arc orbit. In alternative embodiments, the first gantry 110 may comprise a single ring structure, which may be either closed or open. The second gantry 120 carrying the treatment head 130, which will be described in greater detail below, may ride on or move along the circular or arc orbit of the single ring structure of the first gantry.

Referring to FIGS. 1A-1B, the second gantry 120 carries the treatment head 130 and is rotatable about a second axis 116 passing through the isocenter 112, as indicated by arrow 117. Rotating the second gantry 120 about the second axis 116 allows the treatment head 130 to be positioned at a plurality of locations in a second plane, thereby allowing therapeutic radiation to aim at the target volume from a plurality of directions or angles. As shown, the second axis of rotation 116 of the second gantry 120 is non-parallel with the first axis of rotation 114 of the first gantry 110. Therefore, the plurality of locations of the treatment head 130 in the second plane provided by rotation of the second gantry 120 about the second axis 116 are non-coplanar with the plurality of locations of the treatment head 130 in the first plane provided by rotation of the first gantry 110 about the first axis 114. In the exemplary embodiment shown in FIG. 1A, the second axis of rotation 116 of the second gantry 120 may be generally perpendicular to the ring structures 110a, 110b of the first gantry 110. Therefore, the specific direction of the second axis of rotation 116 may depend on the gantry angle of the first gantry 110 and change as the first gantry 110 rotates about the first axis 114, as will be described in greater detail below in conjunction with FIGS. 2A-2D. At a given gantry angle of the first gantry 110, the rotation of the second gantry 120 about the second axis 116 allows the treatment head 130 to be positioned at a plurality of locations in a plane oblique from a transverse or axial plane of the patient 106. For ease of description, the plurality of locations of the treatment head 130 in a plane oblique from a transverse plane of the patient 106 may be collectively referred to as non-coplanar locations.

In the exemplary embodiment shown in FIGS. 1A-1B, the second gantry 120 may be in the form of a truck, frame, bracket, or any other suitable form. The second gantry 120 may ride on the curved rail bearings 138 on the first and second ring structures 110a, 110b of the first gantry 110. The treatment head 130, including the LINAC 132, magnetron 136, and the target, multi-leaf collimator (MLC) and an ion chamber assembly 136, may be mounted to and carried by the second gantry 120. A modulator 137, which provides high voltage pulses to the magnetron 136, may also be mounted to and carried by the second gantry 120. In alternative embodiments, the modulator 137 may be mounted to and carried by the first gantry 110. In the exemplary embodiment shown in FIGS. 1A-1B, the modulator 137 is mounted to the movable stage 144, which rotates the first gantry 110 along the circular rail bearings 146 about the first axis 114. In embodiments where the modulator is coupled to the first gantry 110, cabling between the modulator 137 and treatment head 130 can be properly arranged or configured to accommodate the complete range of motion of the second gantry 120 about the second axis 116.

FIGS. 1A-1B shows a magnetron 134 as an exemplary microwave source carried by the second gantry 120 for illustration purpose. Alternatively, the magnetron 134 may be carried by the first gantry 110. As such, suitable waveguides and rotary joints may be used to couple the microwave energy output from the magnetron carried by the first gantry to the LINAC carried by the second gantry. In some embodiments, a klystron may be used as a microwave source. The klystron may or may not be attached to the radiation system 100. For example, a klystron may be located in a stationary cabinet (not shown) near the radiation system 100. As such, waveguides and rotary joints may be used to couple the microwave energy output from the klystron to the LINAC carried by the second gantry.

The rotation of the second gantry 120 about the second axis 116 may be actuated by a drive system 148. The drive system 148 may drive the second gantry 120 in either direction, clockwise or counterclockwise, allowing the treatment head 130 to deliver therapeutic radiation to the target volume from a plurality of non-coplanar locations.

In the above description in connection with FIGS. 1A-1B, the exemplary first gantry comprises a ring structure and the exemplary second gantry rides on the circular orbit of the ring structure of the first gantry. It should be noted that in some embodiments, the first gantry 110 may comprise one or more beam members which may be rotated about the first axis. The one or more beam members may be either linear or arcuate. The treatment head 130 may be supported by one or more of the beam members. The treatment head may be further linearly translated on the beam member(s) or rotated about a second axis, depending on the shape or configuration of the beam member(s). The linear movement of the treatment head on linear beam member(s) allows the treatment head to be positioned closer to the patient, providing for higher dose rate. This would also allow for more space above the treatment head below the cover of the radiation system so that a larger or more powerful treatment head may be used. In some embodiments, a tilting mechanism may be used to tilt the treatment head, thereby allowing therapeutic radiation to remain aiming at the target volume when the treatment head is positioned at various locations on the linear beam member(s).

FIGS. 2A through 2D illustrate a range of rotations of the first and second gantries in operation. For ease of description, a first coordinate system may be used to describe the gantry angle of the first gantry 110, wherein the point (0, 0, 0) represents the isocenter 112 of the radiation system 100, x-axis represents the first axis of rotation 114 of the first gantry 110 e.g. the patient's superior-inferior direction as shown, z-axis represents the vertical direction passing through the isocenter 112, and y-axis represents the direction perpendicular to the xz plane passing through the isocenter 112. The term "gantry angle" of the first gantry 110, as used heretofore and hereafter, refers to an angular position of the treatment head 130 in the first coordinate system relative to the z-axis as viewed from the x-axis (e.g. end view). A separate, second coordinate system may be used to describe the gantry angle of the second gantry 120, where the point (0', 0', 0') represents the isocenter 112 of the radiation system 100, x'-axis represents the second axis of rotation 116 of the second gantry 120, y'-axis represents the first axis of rotation 114 of the first gantry 110 e.g. the patient's superior-inferior direction as shown passing through the isocenter, and z'-axis represents a direction perpendicular to the x'y' plane passing through the isocenter 112. The term "gantry angle" of the second gantry 120 refers to an angular position of the treatment head 130 in the second coordinate system relative to the z'-axis as viewed from the x'-axis. As described above, the specific direction of the second axis of rotation 116 (x') of the second gantry 120 may depend on the gantry angle of the first gantry 110 and change as the first gantry 110 rotates. Therefore, the x'y' plane and the z' axis of the second coordinate system of the second gantry 120 may also change as the first gantry 110 rotates. However, the angular position of the treatment head 130 relative to the z'-axis as viewed from a direction of the x'-axis does not depend on the rotation of the first gantry 110.

Figure 2A:
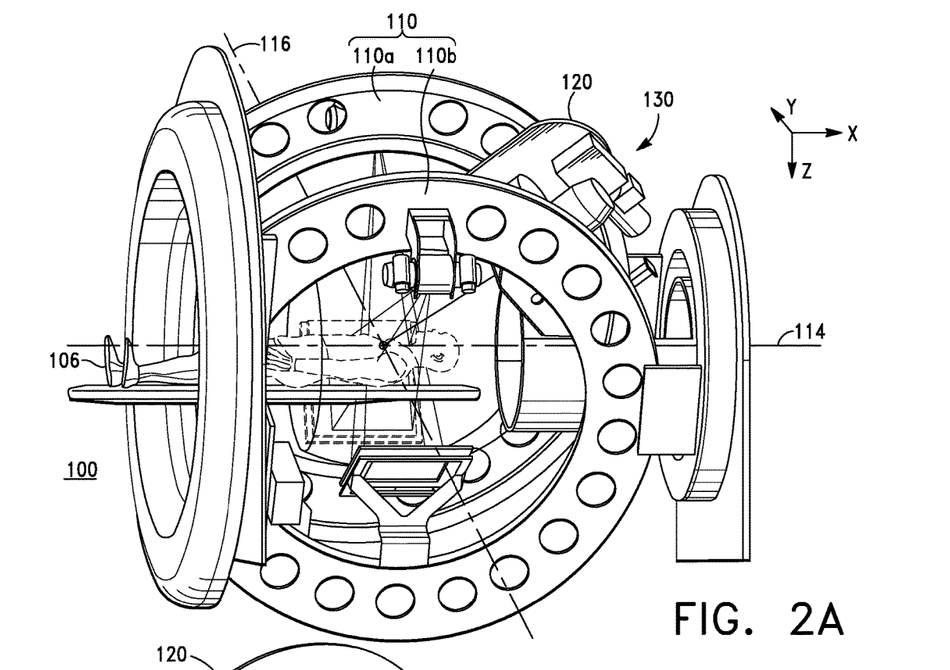
FIGS. 2A-2D illustrate a range of rotations of the radiation system illustrated in FIGS. 1A and 1B.

FIG. 2A illustrates an embodiment where the patient 106 is supported in a supine position head first and the first gantry 110 is located at a gantry angle of zero degree. As the first gantry 110 is located at a gantry angle of zero degree, the second axis of rotation 116 of the second gantry 120 is in the direction of left-right of the patient 106. The second gantry 120 carrying the treatment head 130 rotates about the second axis 116 to position the treatment head 130 at a plurality of locations above the patient 106, thereby allowing therapeutic radiation to aim at the target volume from a plurality of directions or angles above the patient 106. Similarly, in an embodiment where the gantry angle of the first gantry 110 is 180 degrees, the second axis of rotation 116 of the second gantry 120 is also in the direction of left-right of the patient 106. The second gantry 120 carrying the treatment head 130 rotates about the second axis 116 to position the treatment head 130 at a plurality of locations under the patient 106, thereby allowing therapeutic radiation to aim at the target volume from a plurality of directions or angles under the patient 106.

Figure 2B:
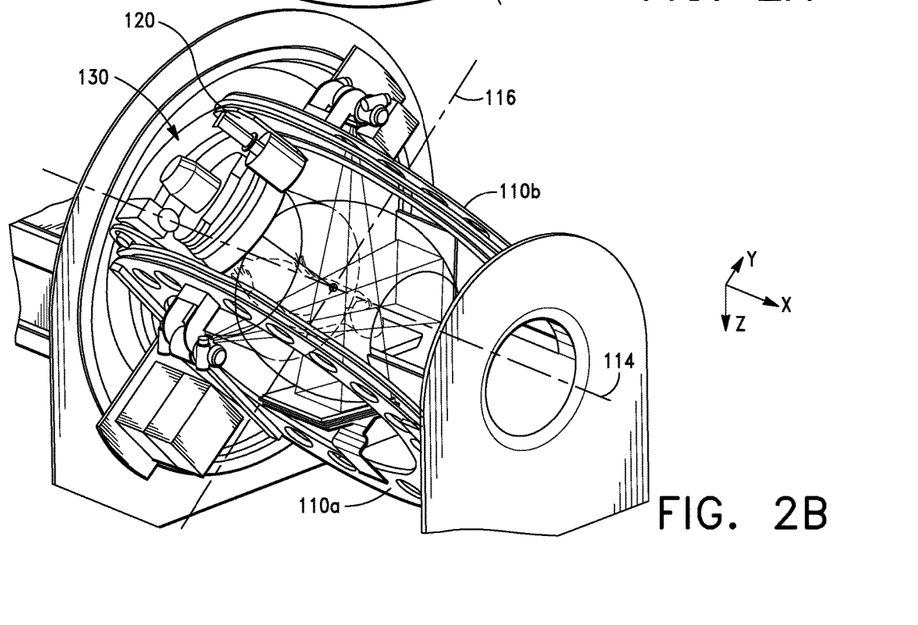

FIG. 2B illustrates an embodiment where the first gantry 110 rotates about the first axis 114 to position the treatment head 130 at a gantry angle of about 45 degrees (counterclockwise viewed from the end). At the gantry angle of 45 degrees of the first gantry 110, the second gantry 120 carrying the treatment head 130 may rotate about a second axis 116, to position the treatment head 130 at one of a plurality of locations. In the embodiment shown in FIG. 2B, the second axis 116 about which the second gantry 120 may rotate has a different direction from that of the second axis shown in FIG. 2A. Therefore, at the gantry angle of 45 degrees (counter-clockwise) of the first gantry 110, the second gantry 120 can position the treatment head 130 at a plurality of additional non-coplanar locations, allowing therapeutic radiation to aim at the target volume from a plurality of additional directions or angles.

Figure 2C:
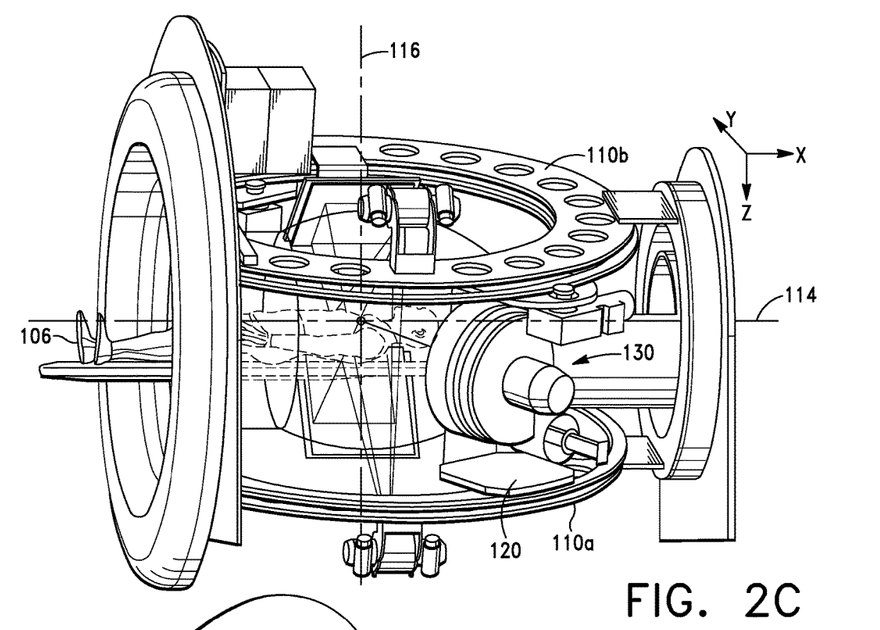

FIG. 2C illustrates an embodiment where the first gantry 110 rotates about the first axis 114 to position the treatment head 130 at a gantry angle of about 90 degrees (counter-clockwise viewed from the end). At the gantry angle of 90 degrees of the first gantry 110, the second gantry 120 carrying the treatment head 130 may rotate about a second axis 116, to position the treatment head 130 at a plurality of locations at a side (e.g. the left side) of the patient 106. In the embodiment shown in FIG. 2C, the second axis 116 of rotation of the second gantry 120 is directed along the anterior-posterior (AP) axis of the patient 106. Similarly, in an embodiment where the gantry angle of the first gantry 110 is 270 degrees (counter-clockwise viewed from the end), the second axis of rotation 116 of the second gantry 120 is also in the direction of anterior-posterior (AP) axis of the patient 106. The second gantry 120 carrying the treatment head 130 rotates about the second axis 116 to position the treatment head 130 at a plurality of locations at the other side (e.g. the right side) of the patient 106, thereby allowing therapeutic radiation to aim at the target volume from a plurality of directions or angles at the right side of the patient 106.

Figure 2D:
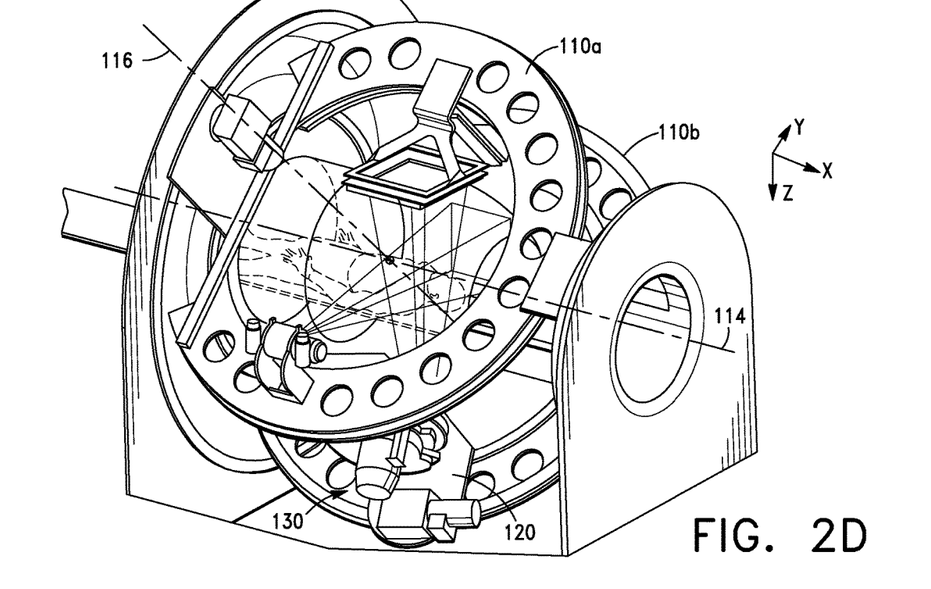

FIG. 2D illustrates an embodiment where the first gantry 110 rotates about the first axis 114 and the treatment head 130 is positioned at a gantry angle of about 135 degrees (counter-clockwise viewed from the end). At the gantry angle of 135 degrees of the first gantry 110, the second gantry 120 carrying the treatment head 130 may rotate about a second axis 116, allowing the treatment head 130 to be positioned at a plurality of locations. In the embodiment shown in FIG. 2D, the second axis 116 has a further different direction. Therefore, at the gantry angle of 135 degrees (counter-clockwise viewed from the end) of the first gantry 110, the second gantry 120 can position the treatment head 130 at a plurality of additional locations, allowing therapeutic radiation to aim at the target volume from a plurality of additional directions or angles.

FIGS. 2A through 2D show that the rotation of the first gantry 110, about the first axis 114 allows the treatment head 130 to be positioned at a plurality of locations in a first plane, allowing therapeutic radiation to aim at the target volume from the plurality of directions or angles. At any particular gantry angle or location in the first plane, the rotation of the second gantry 120 about a second axis 116 allows the treatment head 130 to be positioned at a plurality of locations in a second plane non-coplanar with the first plane, allowing therapeutic radiation to aim at the target volume from a plurality of additional directions or angles. The combination of rotations of the first and second gantries 110, 120 about the first and second axes 114, 116 can provide the treatment head 130 with numerous planar and non-coplanar trajectories around the patient 116 in delivering therapeutic radiation to the target volume.

It should be noted that depending on applications and treatment plans, the first and second gantries 110, 120 can be controlled such that their rotations may be either simultaneous, or sequential in which case either the first gantry 110 can rotate first or the second gantry 120 rotate first. Either rotation of the first and second gantries 110, 120 can be either continuous or discontinuous. The speed of either rotation can be either constant or varied. In case of constant rotations, the speeds of the rotations can be same or different. Indeed, the combination of two axes of rotation provided by the first and second gantries 110, 120 allows the treatment head 130 to be positioned at a wide range of coplanar and non-coplanar locations, thereby allowing therapeutic radiation to aim at the target volume from various angles. Therefore, the term "a second plane" of locations of the second gantry 120 as used in the description and appended claims include reference to a plurality of planes as the second gantry 120 may rotate about the second axis when the first gantry changes its locations. Conversely, the term "a first plane" of locations of the first gantry 110 as used in the description and appended claims include reference to a plurality of planes as the first gantry 110 may rotate about the first axis when the second gantry changes its locations.

Returning to FIGS. 1A-1B, the exemplary radiation system 100 may include one or more imaging systems. As shown, a first imaging system 122 comprises an imaging source 122a and an imager 122b. A second imaging system 124 comprises an imaging source 124a and an imager 124b. The first and second imaging systems 122, 124 may be coupled to the first gantry 110 and thus are rotatable about the first axis 114. Alternatively or additionally, an imaging system may be coupled to the second gantry 120 and is thus further rotatable about the second axis 116. The first and second imaging sources 122a, 124a may be a radiation source producing x-rays having an energy level at kilovolts (kV). The first and second imagers 122b, 124b may be a flat panel imager known in the art.

The first and/or second imaging systems 122, 124 can be configured to allow for acquisition of cone-beam computed tomography (CBCT) data for patient set-up and/or adaptive treatment planning. The first and/or second imaging systems 122, 124 can also be used to acquire projection radiographs or digital tomosynthesis data before treatment for patient set-up or adaptive planning. Alternatively or additionally, the first and/or second imaging systems 122, 124 may be configured to acquire imaging data during treatment for intrafraction motion management. CBCT, tomosynthesis, and imaging guided radiotherapy (IGRT) are known in the art and therefore their detailed description is omitted herein for clarity of description of embodiments of the disclosure.

Still referring to FIGS. 1A-1B, in the exemplary radiation system 100 as shown, the imaging source 122a of the first imaging system 122 can be mounted to a side surface of the first ring structure 110a of the first gantry 110 via a mount and the paired imager 110b can be mounted to a side surface of the second ring structure 110b of the first gantry 110 via a mount. The imaging source 124a of the second imaging system 124 can be mounted to a side of the second ring structure 110b of the first gantry 110 via a mount and the paired imager 124b can be mounted to a side of the first ring structure 110a via a mount. Therefore, when viewed from an end along the direction of the first axis 114 (FIG. 1B), the imaging sources 122a, 124a of the first and second imaging systems 122, 124, or the central beam lines of the first and second sources 122a, 124a, form a non-zero angle (theta) subtended from the isocenter 112. The angle (theta) can be 45, 60, 90, 120, or 180 degrees, or any angle between 45 and 180 degrees. By spacing apart and operating the imaging source-imager pairs 122, 124 simultaneously, it is possible to reduce the rotation angle of the first gantry 110 required for acquiring an adequate set of CBCT data. In some embodiments, one or both of the imagers 122b, 124b of the first and second imaging systems 122, 124 is (are) laterally movable relative to one or both of respectively paired imaging sources 122a, 124a. Motion axes including motors, moving stages, guide, guide rails, or any other suitable mechanisms may be used to move the imagers on the mounts. The capability of lateral shifting of the imagers 122b, 124b relative to their respective imaging sources 122a, 124a enables acquisition of data in "half-fan mode" to enlarge the field-of-view (FOV) of the imaging systems. In alternative embodiments, the imagers 122b, 124b may be rigidly mounted to provide absolute position information of the patient 106 with respect to the overall radiation system 100 and better correction for patient support sag or tilting etc.

In the embodiments shown in FIGS. 1A and 1B, the imaging sources 122a, 124a of the first and second imaging systems 122, 124 may be fixedly mounted to the first and second ring structures 110a, 110b. As such, the angle (theta) between the imaging sources 122a, 124a, as viewed from an end along the direction of the first axis 114, is fixed. In alternative embodiments, the angle between imaging sources of the first and second imaging systems, as viewed along the direction of the first axis, is adjustable, as shown in FIGS. 4A and 4B.

Figure 4A:
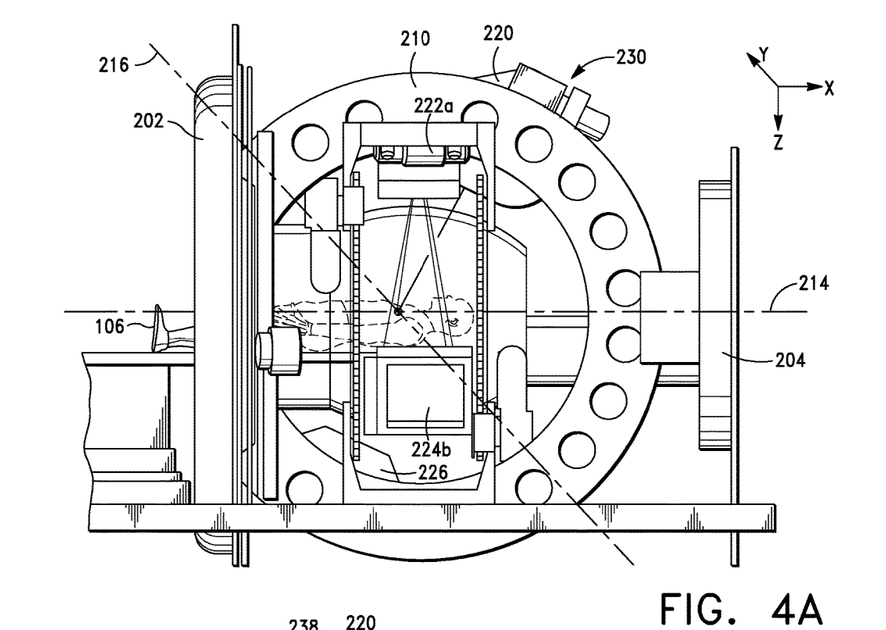
FIG. 4A illustrates a side view of an exemplary radiation system according to alternative embodiments of the disclosure.
Figure 4B:
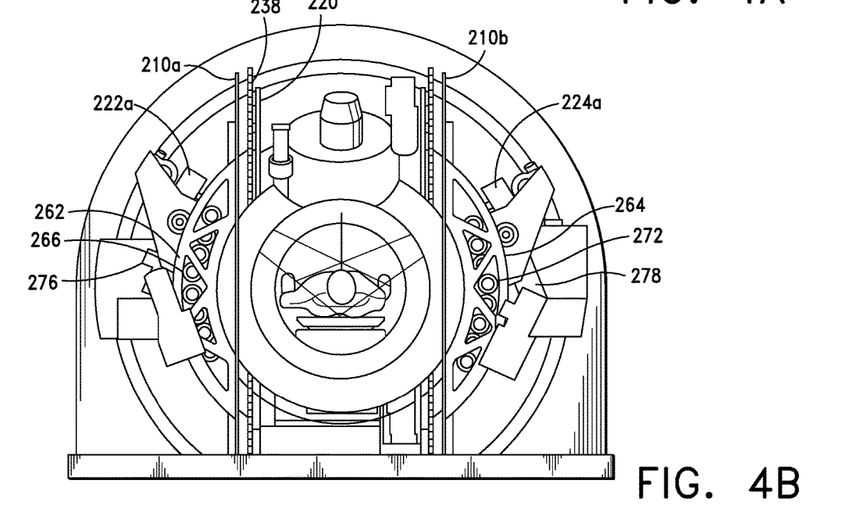
FIG. 4B illustrates an end view of the radiation system illustrated in FIG. 4A.

Referring to FIGS. 4A and 4B, the exemplary radiation system 200 is similar to the radiation system 100 shown in FIGS. 1A and 1B in many aspects. For example, the radiation system 200 may include a first gantry 210 comprising a first ring structure 210a and a second ring structure 210b rotatably supported by a first support 202 and a second support 204, a second gantry 220 riding on curved rail bearings 238 mounted on the first and second ring structures 210a, 210b, and a treatment head 230 carried by the second gantry 220. The first gantry 210 is rotatable about a first axis 214 passing through the isocenter 212. The second gantry 220 carrying the treatment head 230 is rotatable about a second axis 216 passing through the isocenter 212. The radiation system 200 may also include a first imaging system 222 comprising an imaging source 222a, a second imaging system 224 comprising an imaging source 224a, and an EPID 226 disposed opposite to the treatment head 230.

In comparison with the radiation system 100 shown in FIGS. 1A and 1B, the radiation system 200 shown in FIGS. 4A and 4B allows the non-zero angle between the imaging sources 222a, 224a to be adjustable. As shown, the radiation system 200 shown in FIGS. 4A and 4B comprises a first arcuate structure 262 and a second arcuate structure 264 to allow the first and second imaging sources 222a, 224a to be movable. For example, curved rail bearings 266 on the first arcuate structure 262 allow the first imaging source 222a to move along a curved orbit. Curved rail bearings 272 on the second arcuate structure 264 allow the second imaging source 224a to move along a curved orbit. Drives 276, 278 operate to move the imaging sources 222a, 224a respectively. By moving the imaging sources 222a, 224a over the curved rail bearings, the angle between the first and second imaging source 222a, 224a, as viewed from an end along the direction of the first axis 214, can be adjusted. The first and second arcuate structures 262, 264 may be mounted to the first and second ring structures 210a, 210b of the first gantry 210 respectively. Therefore, the first and second imaging sources 222a, 224a supported by the first and second arcuate structures 262, 264 may be rotatable with the first gantry 210. In an exemplary embodiment, the first and second arcuate structures 262, 264 may be configured such that the first and second imaging sources 222a, 224a are movable in the plane generally perpendicular to the moving plane of treatment source 230. As such, the first and second imaging sources 222a, 224a may further rotate with the first gantry 210 around the first axis 214. Alternatively, the first and second arcuate structures 262, 264 may be arranged or oriented such that the first and second imaging sources 222a, 224a may rotate around axes non-parallel with the first axis 214. While not shown in FIG. 1B for clarity, the first and second imaging systems 222, 224 may comprise imagers paired with imaging sources 222a, 224a respectively. The imagers can generally move in concert with their paired imaging sources 222a, 224a.

Returning to FIGS. 1A and 1B, the radiation system 100 may include an electronic portal imaging device (EPID) 126 for acquiring images with the treatment source 130. The EPID 126 may be coupled to or rigidly tied to the second gantry 120 in a position opposite to the treatment head 130. As such, the EPID 126 and the treatment head 130 can be moved together with the second gantry 120 about the second axis 116 using a single drive. In some embodiments shown in FIGS. 1A-1B, a separate truck 152 may be used to carry and position the EPID 126 relative to the treatment head 130. In operation, an EPID 126 is positioned 180 degrees from the treatment head 130. In some embodiments, a greater range of source motions may be desired to achieve large caudal and/or cranial angles. Therefore, it may be advantageous that the EPID 126 not be positioned opposite the treatment head 130 at all times. Hence, the separate truck 152, powered by a separate drive system 154 is advantageous by giving the system maximum flexibility of motion allowing the trucks to independently avoid interferences with obstacles, e.g. either the inner bore or the first or second gantries, as will be described in greater below. In the embodiment where the treatment head 130 and EPID 126 are carried separately, extra interlocks and position sensing devices e.g. shaft encoders, potentiometers, or the like, may be incorporated into the system to ensure that the EPID 126 and treatment head 130 are accurately aligned or where they should be. A beamstop 156 for blocking or attenuating radiation penetrating through the patient 106 and EPID 126 may be carried by the truck 152. In some preferred embodiments, the EPID 126 and beamstop 156 assembly can be shifted laterally relative to the treatment head 130 using suitable motion axes for half-fan CBCT acquisitions to enlarge the FOV.

Figure 3A:
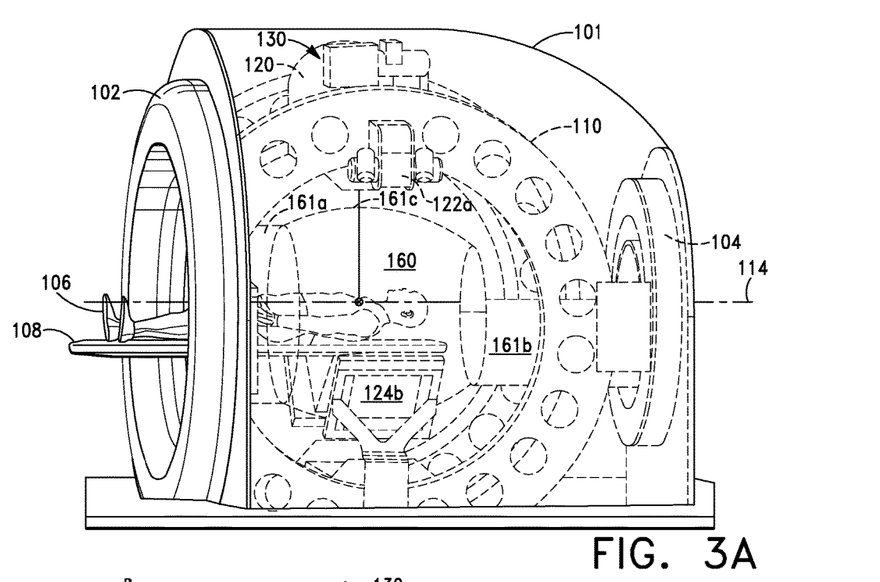
FIG. 3A illustrates a side view of an exemplary radiation system according to embodiments of the disclosure, showing an enclosure covering the system.
Figure 3B:
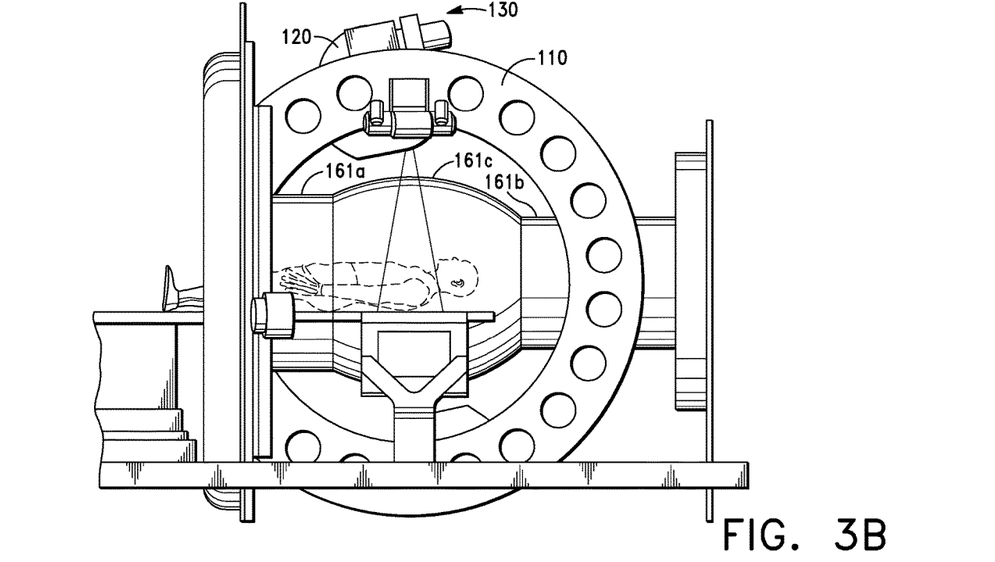
FIG. 3B illustrates a side view of an exemplary radiation system according to embodiments of the disclosure, showing an inner bore of the system.

Referring now to FIGS. 3A and 3B, the radiation system 100 may include an enclosure 101 that encloses the first gantry 110, the second gantry 120, the treatment head 130, and other devices such as imaging systems 122, 124 and EPID 126. The enclosure 101 protects the patient 106 from the inner workings of the gantries and devices and presents a cosmetically pleasing environment. The enclosure 101 may also be configured to provide soundproofing and/or block at least some of the radiation resulted from an operation of the radiation source.

As shown, the enclosure 101 defines an inner bore 160 along the first axis 114 to allow at least a portion of the patient 106 to extend therethrough. Alternatively or in addition, the inner bore 160 can be defined by a generally tubular structure 161, which may include one or more sections.

An exemplary tubular structure 161 shown in FIGS. 3A and 3B may include multiple sections, e.g., a first end section 161a, a second end section 161b, and a middle section 161c between the first and second end sections. As shown, the first and second end sections 161a, 161b may be in the form of cylinders, which may have a same or different radius. The middle section 161c may bulge out at the isocenter plane to permit for a more open feel.

In some embodiments, the first or second end section 161a, 161b of the tubular structure 161 may be designed such that at least a portion can be moved out of the way to allow the second gantry 120 carrying the treatment head 130 to move into the area occupied or enclosed by the portion moved out. For example, a portion of the second end section 161b can be slid in or out of the way along the superior direction (in cases when the patient is laying head first). In some embodiments, the second end section 161b may include two hemi-cylindrical components which can be rotated against each other along the first axis 114. The rotation of the hem i-cylindrical components opens up the inner bore 160, thereby allowing the second gantry 120 carrying the treatment head 130 to move into the area occupied or enclosed by one of the hemi-cylindrical components. The hemi-cylindrical components may be coupled to an end bearing support and rotate in tandem with the first and second ring structures 110a, 110b of the first gantry 110. By way of example, in embodiments where the second end section 161b (adjacent the patient head) consists of two hemi-cylindrical components and is closed, a cranial non-coplanar angle of the treatment head 130 (with the second gantry) of about 38 degree can be obtained. When the second end section 161b is opened e.g. by rotating the hemi-cylindrical components, a cranial non-coplanar angle of about 60 to 90 degrees can be obtained. This allows the treatment head 130 to be positioned directly above the patient's head in the superior direction.

The enclosure 101 may include a shielding material configured to block at least some of the radiation resulted from an operation of the radiation source. In some embodiments, the enclosure 101 may be made of the shielding material. In other embodiments, the shielding material may be coupled to the enclosure 101. For example, the shielding material may be coupled to an outside surface of the enclosure 101, an inside surface of the enclosure 101, or may be in the form of one or more layers embedded within the enclosure 101. The shielding material may be configured, e.g. by way of certain material density, certain geometry, and/or certain thickness, to block radiation so that it reduces at least 98% and more preferably at least 99.9%, and even more preferably at least 99.999%, of the radiation such as photons, electrons, neutrons, or other charged particles etc. resulted from an operation of the radiation source traveling therethrough. The shielding material may be configured to block off a sufficient amount of radiation resulted from an operation of the radiation source so that it eliminates the need for shielding a facility building, such as at a hospital. Such a feature is advantageous because it allows the radiation system to be useable at any location within the building, or at any facility, without requiring expensive retrofit to be done to the building to provide radiation shielding. Alternatively, the shielding material may be configured to block off a sufficient amount of radiation resulted from an operation of the radiation source so that it reduces a significant amount e.g., at least 50%, and more preferably, at least 90% of the shielding requirement at a building. Such a feature is advantageous because it allows the radiation system to be useable at any location within the building, or at any facility, with minimal retrofit to be done to the building to provide radiation shielding.

In some embodiments, the enclosure 101 may be further configured to provide a soundproof environment. For example, a soundproof cover or barrier may be coupled to an inside surface of the enclosure or an outside surface of the enclosure, to absorb or reduce the noise resulting from an operation of the radiation machine. By way of example, a soundproof cover may include a porous absorbing material e.g. open cell rubber foams or melamine sponges which can absorb noise. A soundproof cover may also include resonant panels or absorbers which can damp noise.

Returning to FIGS. 1A-1B, the exemplary radiation system 100 as shown comprises a first support 102 at the front or first end and a second support 104 at the rear or second end. The first and second supports 102, 104 may be fixedly secured e.g. to the floor or ceiling of a treatment room, and configured to rotatably support the first and second ring structures 110a, 110b of the first gantry 110. By way of example, rail bearings 146 may be mounted on the first and/or second supports 102, 104, allowing the first gantry 110, and thus the second gantry 120 carrying the treatment head 130, to rotate about the first axis 114. In alternative embodiments, the first gantry 110 may be rotatably supported by a single end support. Using a single support may reduce the total bore length and the costs of making the system. The single support may be located at either the front or rear end.

Still referring to FIGS. 1A and 1B, the first support 102 may have an annular ring configuration having an opening to allow the patient to extend through into the inner bore of the system. As such, the annular ring of the first support 102 may be oriented to be substantially perpendicular to the first and second ring structures 110a, 110b of the first gantry 110. The first and second ring structures 110a, 110b of the first gantry 110 may be spaced apart to accommodate the patient 106 extending through the opening in the first support 102. Alternatively or in addition, the second support 104 may also have an annular ring configuration. The annular ring of the second support 104 may be oriented to be substantially perpendicular to the first and second ring structures 110a, 110b of the first gantry 110. The annular ring configuration of the second support 104 allows a section of the inner bore structure to be slid in or out of the way along the first axis of rotation 114, allowing the second gantry 120 to move into the area occupied or enclosed by the portion moved out, leading to increased cranial non-coplanar angle of the treatment head 130, as described above. In alternative embodiments described above, a section of the inner bore structure may include two hemi-cylinders that rotate against each other along the first axis 114 (superior-inferior direction of the patient). As such, the hemi-cylinders can be coupled to the second support 104 and rotate in tandem with the rings 110a, 110b of the first gantry 110 to allow for a multiplicity of rotation angles along the first axis 114 to be obtained.

In any of the embodiments disclosed herein, the radiation system may further include a patient monitoring system. The patient monitoring system may include an optical device such as a CCD camera or other type of optical sensor capable of sensing an object. The optical device may be mounted to the radiation system e.g. within the bore, to the patient support, to a ceiling, or to a suitable support stand. In some embodiments, a marker or markers may be attached to the patient or patient support to be viewed or sensed by the optical device. The markers can be implemented using reflective objects. The image signals received from the optical device may be processed and used by the control of the radiation system for an operation of the radiation system Embodiments of a radiation system have been described. Those skilled in the art will appreciate that various other modifications may be made within the spirit and scope of the invention. All these or other variations and modifications are contemplated by the inventors and within the scope of the invention.

What is claimed is:

1. A radiation system, comprising:
a radiation source providing therapeutic radiation;
a first gantry supporting a second gantry carrying the radiation source, the first gantry being rotatable about a first axis passing through an isocenter, thereby allowing the radiation source carried by the second gantry to aim therapeutic radiation at a target volume from a plurality of locations in a first plane;
the second gantry carrying the radiation source, the second gantry being rotatable about a second axis passing through the isocenter non-parallel with the first axis, thereby allowing the radiation source to aim therapeutic radiation at the target volume from a plurality of locations in a second plane non-coplanar with the first plane, wherein
the first gantry comprises a ring structure substantially in parallel with the first axis, and
the second gantry is moveable on the ring structure to rotate about the second axis substantially perpendicular to the ring structure.

2. The radiation system of claim 1, wherein the ring structure of the first gantry comprises:
a first ring and a second ring spaced apart from each other and substantially in parallel with the first axis, and
guides mounted on the first and second rings, wherein the second gantry rides on the guides to rotate about the second axis.

3. The radiation system of claim 1, further comprising a support rotatably supporting the first gantry, the support comprising an annular ring structure substantially perpendicular to the ring structure of the first gantry.

4. The radiation system of claim 3, wherein the ring structure of the first gantry comprises:
a first ring and a second ring spaced apart from each other and substantially in parallel with the first axis, and
guides mounted on the first and second rings, wherein the second gantry rides on the guides to rotate about the second axis.

5. The radiation system of claim 3, wherein the annular rind structure of the support comprises a first annular ring structure and a second annular ring structure substantially perpendicular to the ring structure of the first gantry, wherein the ring structure of the first gantry is rotatably supported by the first annular ring structure of the support at a first end and by the second annular ring structure of the support at a second end.

6. The radiation system of claim 5, wherein the ring structure of the first gantry comprises:
a first ring and a second ring spaced apart from each other and substantially in parallel with the first axis, and
guides mounted on the first and second rings, wherein the second gantry rides on the guides to rotate about the second axis.

7. The radiation system of claim 1, further comprising an imaging system including an imaging source and an imager, wherein the imaging source and the imager of the imaging system are arranged such that radiation from the imaging source and therapeutic radiation from the radiation source form an angle of about 90 degrees.

8. The radiation system of claim 1, further comprising an imaging system including an imaging source and an imager, wherein the imaging source is coupled to the second gantry and located adjacent to and movable with the radiation source to provide beam's eye view imaging.

9. The radiation system of claim 1, further comprising:
a first imaging system comprising an imaging source and an imager coupled to the ring structure of the first gantry; and
a second imaging system comprising an imaging source and an imager coupled to the ring structure the first gantry, wherein
the imaging sources of the first and second imaging systems are located such that radiation beams from the imaging sources of the first and second imaging systems form a non-zero angle subtended from the isocenter as viewed along the first axis.

10. The radiation system of claim 9, wherein a position of the imaging source of the first and/or second imaging systems is adjustable such that the non-zero angle formed between radiation beams from the first and second imaging sources is adjustable.

11. The radiation system of claim 9, further comprising a detector configured to generate an image with therapeutic radiation from the radiation source, wherein the detector is movable independent of the second gantry carrying the radiation source.

12. The radiation system of claim 9, further comprising a third imaging system including an imaging source and an imager, wherein the imaging source of the third imaging system is coupled to the second gantry and located adjacent to and movable with the radiation source.

13. A radiation system comprising:
a radiation source providing therapeutic radiation;
a first gantry supporting a second gantry carrying the radiation source, the first gantry being rotatable about a first axis passing through an isocenter, thereby allowing the radiation source carried by the second gantry to aim therapeutic radiation at a target volume from a plurality of locations in a first plane;
the second gantry carrying the radiation source, the second gantry being rotatable about a second axis passing through the isocenter non-parallel with the first axis, thereby allowing the radiation source to aim therapeutic radiation at the target volume from a plurality of locations in a second plane non-coplanar with the first plane,
further comprising an enclosure enclosing the first gantry, the second gantry, and the radiation source, wherein a portion of the enclosure defines an inner bore along the first axis to accommodate at least a portion of a subject containing the target volume, wherein the portion of the enclosure defining the inner bore comprises a generally tubular structure, at least a portion of the generally tubular structure is removable to allow the second gantry carrying the radiation source to move into a space occupied or enclosed by the portion of the tubular structure.

14. The radiation system of claim 13, wherein the generally tubular structure comprising a first end section, a second end section, and a middle section between the first and second sections, wherein the first and second sections are generally cylindrical, and the third section bulges out in a plane passing through the isocenter.

15. The radiation system of claim 14, wherein at least one of the first and second sections comprises a first hemi-cylindrical component and a second hemi-cylindrical component, wherein the first and second hemi-cylindrical components are rotatable against each other to open the generally tubular structure, thereby allowing the second gantry carrying the radiation source to move into a space occupied or enclosed by the first or second hemi-cylindrical component.

16. A radiation system, comprising:
a radiation source providing therapeutic radiation; and
a gantry operable to rotate the radiation source to a plurality of locations relative to a target volume at an isocenter, wherein
the gantry comprises a ring structure rotatable about a first axis that is substantially in parallel with the ring structure and passes through the isocenter, wherein rotation of the ring structure about the first axis allows the radiation source to aim therapeutic radiation at the target volume from a plurality of locations in a first plane,
the radiation source is moveable on the ring structure and rotatable about a second axis that is substantially perpendicular to the ring structure and passes through the isocenter, wherein rotation of the radiation source about the second axis allows the radiation source to aim therapeutic radiation at the target volume from a plurality of locations in a second plane non-coplanar with the first plane, and
an enclosure enclosing the radiation source and the gantry, wherein a portion of the enclosure defines an inner bore along the first axis to accommodate at least a portion of a subject containing the target volume.

17. The radiation system of claim 16, further comprising an imaging system including an imaging source and an imager coupled to the gantry, wherein the imaging source and the imager of the imaging system are arranged such that radiation from the imaging source and therapeutic radiation from the radiation source form an angle of about 90 degrees.

18. The radiation system of claim 16, further comprising an imaging system including an imaging source and an imager coupled to the gantry, wherein the imaging source is located adjacent to and movable with the radiation source to provide beam's eye view imaging.

19. The radiation system of claim 16, wherein the portion of the enclosure defining the inner bore comprises a generally tubular structure, at least a section of the generally tubular structure is removable to allow the radiation source to move into a space occupied or enclosed by the section removed.

20. The radiation system of claim 16, wherein the portion of the enclosure defining the inner bore comprises a generally tubular structure, the generally tubular structure comprising a first end section, a second end section, and a middle section between the first and second sections, wherein the first and second end sections are generally cylindrical, and the third section bulges out in a plane passing through the isocenter.

21. The radiation system of claim 20, wherein at least one of the first and second end sections comprises a first hemi-cylindrical component and a second hemi-cylindrical component, wherein the first and second hemi-cylindrical components are rotatable against each other to open the generally tubular structure, thereby allowing the radiation source to move into a space occupied or enclosed by the first or second hemi-cylindrical component.

22. A radiation system, comprising:
a radiation source providing therapeutic radiation; and
a gantry operable to rotate the radiation source to a plurality of locations relative to a target volume at an isocenter, wherein
the gantry comprises a ring structure rotatable about a first axis that is substantially in parallel with the ring structure and passes through the isocenter, wherein rotation of the ring structure about the first axis allows the radiation source to aim therapeutic radiation at the target volume from a plurality of locations in a first plane,
the radiation source is moveable on the ring structure and rotatable about a second axis that is substantially perpendicular to the ring structure and passes through the isocenter, wherein rotation of the radiation source about the second axis allows the radiation source to aim therapeutic radiation at the target volume from a plurality of locations in a second plane non-coplanar with the first plane,
wherein the ring structure comprises:
a first ring and a second ring spaced apart from each other and substantially in parallel with the first axis, and
guides mounted on the first and second rings,
wherein the radiation source is moveable over the guides to rotate about the second axis.

23. The radiation system of claim 22, further comprising:
a first imaging system comprising an imaging source coupled to the first ring and an imager coupled to the second ring; and
a second imaging system comprising an imaging source coupled to the second ring and an imager coupled to the first ring, wherein
the imaging sources of the first and second imaging systems are positioned such that radiation beams from the imaging sources of the first and second imaging systems form a non-zero angle subtended from the isocenter as viewed along the first axis.

24. The radiation system of claim 23, wherein a position of the imaging source and/or imager of the first and/or the second imaging systems is adjustable such that the non-zero angle formed between the radiation beams from the first and second imaging sources is adjustable.

25. The radiation system of claim 23, wherein the imager of the first and/or the second imaging systems is laterally movable relative to the corresponding imaging source of the first and/or the second imaging systems.

26. The radiation system of claim 23, further comprising a third imaging system including an imaging source and an imager, wherein the imaging source of the third imaging system is located adjacent to and movable with the radiation source.

27. The radiation system of claim 23, further comprising a detector configured to generate an image with therapeutic radiation from the radiation source.

28. The radiation system of claim 27, wherein the detector is independently movable relative to the radiation source.

29. The radiation system of claim 27, wherein the detector is laterally movable relative to the radiation source.

30. A radiation system, comprising:
a radiation source providing therapeutic radiation; and
a gantry operable to rotate the radiation source to a plurality of locations relative to a target volume at an isocenter, wherein
the gantry comprises a ring structure rotatable about a first axis that is substantially in parallel with the ring structure and passes through the isocenter, wherein rotation of the ring structure about the first axis allows the radiation source to aim therapeutic radiation at the target volume from a plurality of locations in a first plane,
the radiation source is moveable on the ring structure and rotatable about a second axis that is substantially perpendicular to the ring structure and passes through the isocenter, wherein rotation of the radiation source about the second axis allows the radiation source to aim therapeutic radiation at the target volume from a plurality of locations in a second plane non-coplanar with the first plane, further comprising a support rotatably supporting the gantry, wherein the support comprises an annular ring structure arranged substantially perpendicular to the ring structure of the gantry.

31. The radiation system of claim 30, wherein the ring structure of the gantry comprises:
 a first ring and a second ring spaced apart from each other and substantially in parallel with the first axis, and
 guides mounted on the first and second rings, wherein the radiation source rides over the guides to rotate about the second axis.

32. The radiation system of claim 30, wherein the support comprises a first support having an annular ring structure and a second support having an annular ring structure, wherein the ring structure of the gantry is rotatably supported by and substantially perpendicular to the annular ring structures of the first and second supports.

33. The radiation system of claim 32, wherein the ring structure of the first gantry comprises:
 a first ring and a second ring spaced apart from each other and substantially in parallel with the first axis, and
 guides mounted on the first and second rings, wherein the radiation source rides over the guides to rotate about the second axis.

\* \* \* \* \*

UNITED STATES PATENT AND TRADEMARK OFFICE
CERTIFICATE OF CORRECTION

PATENT NO. : 10,406,382 B2
APPLICATION NO. : 15/494046
DATED : September 10, 2019
INVENTOR(S) : David Humber et al.

Page 1 of 1

It is certified that error appears in the above-identified patent and that said Letters Patent is hereby corrected as shown below:

In the Specification

At Column 3 Line 15, replace "hem i-cylinders" with -- hemi cylinders --.

In the Claims

In Claim 5 at Line 2, replace "rind" with -- ring --.

Signed and Sealed this
Twelfth Day of November, 2019

Andrei Iancu
*Director of the United States Patent and Trademark Office*